US009476027B2

(12) United States Patent
Buelow

(10) Patent No.: US 9,476,027 B2
(45) Date of Patent: Oct. 25, 2016

(54) ENHANCED EXPRESSION OF HUMAN OR HUMANIZED IMMUNOGLOBULIN IN NON-HUMAN TRANSGENIC ANIMALS

(75) Inventor: Roland Buelow, Palo Alto, CA (US)

(73) Assignee: Roche Diagnostics GMBH (DE)

( * ) Notice: Subject to any disclaimer, the term of this patent is extended or adjusted under 35 U.S.C. 154(b) by 528 days.

(21) Appl. No.: 12/972,290

(22) Filed: Dec. 17, 2010

(65) Prior Publication Data

US 2011/0093963 A1    Apr. 21, 2011

Related U.S. Application Data

(63) Continuation of application No. 11/895,910, filed on Aug. 27, 2007, now abandoned.

(60) Provisional application No. 60/841,980, filed on Sep. 1, 2006.

(51) Int. Cl.
| | |
|---|---|
| A01K 67/00 | (2006.01) |
| A01K 67/027 | (2006.01) |
| C12N 15/00 | (2006.01) |
| C07H 21/04 | (2006.01) |
| C12N 5/0781 | (2010.01) |
| A61K 39/00 | (2006.01) |
| C07K 14/705 | (2006.01) |
| C09K 5/04 | (2006.01) |
| C12N 15/85 | (2006.01) |
| C12N 15/79 | (2006.01) |

(52) U.S. Cl.
CPC ......... *C12N 5/0635* (2013.01); *A01K 67/0278* (2013.01); *A61K 39/00* (2013.01); *C07K 14/70503* (2013.01); *C09K 5/045* (2013.01); *C12N 15/8509* (2013.01); *A01K 67/0275* (2013.01); *A01K 67/0276* (2013.01); *A01K 2207/15* (2013.01); *A01K 2217/052* (2013.01); *A01K 2217/054* (2013.01); *A01K 2217/072* (2013.01); *A01K 2227/107* (2013.01); *A01K 2267/01* (2013.01); *C07H 21/04* (2013.01); *C09K 2205/126* (2013.01); *C12N 15/79* (2013.01); *C12N 2510/02* (2013.01); *C12N 2517/02* (2013.01)

(58) Field of Classification Search
CPC ..................... A01K 67/0275; A01K 67/0276; A01K 67/0278; A01K 2207/15; A01K 2217/052; A01K 2217/054; A01K 2227/107; C12N 5/0635; C12N 15/79; C07H 21/04
USPC ....... 800/13, 14; 435/320.1; 536/23.53, 24.1
See application file for complete search history.

(56) References Cited

U.S. PATENT DOCUMENTS

| | | | |
|---|---|---|---|
| 4,554,101 A | 11/1985 | Hopp | |
| 4,977,081 A | 12/1990 | Raybould et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,570,429 A | 10/1996 | Paddock | |
| 5,814,318 A | 9/1998 | Lonberg et al. | |
| 6,706,289 B2 | 3/2004 | Lewis et al. | |
| 7,064,244 B2 | 6/2006 | Jakobovits et al. | |
| 2003/0017534 A1 | 1/2003 | Buelow et al. | |
| 2006/0026696 A1 | 2/2006 | Buelow et al. | |

FOREIGN PATENT DOCUMENTS

| | | |
|---|---|---|
| EP | 0 491 057 B1 | 6/1992 |
| EP | 0 583 980 A1 | 2/1994 |
| WO | WO 92/03918 | 3/1992 |
| WO | WO 96/33735 | 10/1996 |
| WO | WO 97/16537 | 5/1997 |
| WO | WO 99/57268 | 11/1999 |
| WO | WO 01/09187 | 2/2001 |
| WO | WO 02/12437 | 2/2002 |
| WO | WO/02/006618 | 8/2002 |
| WO | WO 2004/071408 A2 | 8/2004 |
| WO | WO 2005/007696 A2 | 1/2005 |

OTHER PUBLICATIONS

Jakobovits et al., 2007, Nature Biotechnology, vol. 25, No. 10, p. 1134-1143.*
Houdebine, L-M., 2002, Journal of Biotechnology, vol. 98, p. 145-160.*
Mercier et al., 1997, "The modification of milk protein composition through transgenesis: progress and problems," In: Transgenic Animals: Generation and use, Ed. Houdebine LM, Harwood Academic Publishers, The Netherlands pp. 473-482.*
Goldman et al., 2004, Med Sci Monit, vol. 10, No. 11, RA274-285.*
Sigmund, C., Jun. 2000, Arterioscler. Thromb. Vasc. Biol., p. 1425-1429.*
Adachi, T., et al., The EMBO Journal—15(7):1534-1541 (1996).
Andris-Widhopf, J., et al., J. Immunol. Methods—242:159-181 (2000).
Bruggemann, M., et al., Curr. Opin. Biotechnot.—8(4):455-458 (1997).

(Continued)

*Primary Examiner* — Shin Lin Chen

(74) *Attorney, Agent, or Firm* — Alexander Skolaut; Ginger R. Dreger; Arnold & Porter LLP

(57) ABSTRACT

The present invention describes transgenic animals with human(ized) immunoglobulin loci and transgenes encoding human(ized) Igα and/or Igβ sequences. Of particular interest are animals with transgenic heavy and light chain immunoglobulin loci capable of producing a diversified human(ized) antibody repertoire that have their endogenous production of Ig and/or endogenous Igα and/or Igβ sequences suppressed. Simultaneous expression of human(ized) immunoglobulin and human(ized) Igα and/or Igβ results in normal B-cell development, affinity maturation and efficient expression of human(ized) antibodies.

3 Claims, 2 Drawing Sheets

(56) References Cited

OTHER PUBLICATIONS

Bruggemann, M., et al., Year in Immunol.,—7:33-40 (1993).
Burton, D. R., "Phage display," Immunotechnology—1:87-94 (1995).
Chang et al. Geneseq Accession No. AAQ24890, computer printout, pp. 3 and 4, (1992).
Cragg, M.S., et al., Blood—100(9):3068-3076 (2002).
Cronin, F.E., et at, J. Immunology—161: 252-259 (1998).
Davies et al., Geneseq Accession No. ADR68273, computer printout, p. 4, (2004).
Fan, J., et al, Pathol. Int.—49:583-594 (1999).
Flaswinkel, H., et al., Immunogenetics—36 (4):266-269 (1992).
Fuentes-Panana, E.M., et al., J. Immunology—174:1245-1252 (2005).
Gauld, S.B., et al., Science—296 5573: 1641-1642 (2002).
Herren, B., et al., Immunologic Res.—26(1-3):35-43 (2002).
Jakobovits, A., et al, Nature—362:255-258 (1993).
Jakobovits, A., et al, Proc. NatL Acad. Sci USA—90:2551-2555 (1993).
Jones, P.T., et al, Nature—321:522-525 (1986).
Kashiwamura, S., et al, The Journal of Immunology—145(1): 337-343, (1990).
Kaye et al., Proc. Natl. Acad. Sci. USA, vol. 87, pp. 6922-6926, (1990).
Koyama, M., et al, Immunology Letters—47(3):151-156 (1995).
Kraus, M., et al., Cell—117(6):787-800 (2004).
Kuroiwa, Y., et al, Nature Biotech—20(9):889-894 (2002).
Kuroiwa, Y., et al., Nature Genetics—36(7):775-480 (2004).
Lonberg, N., et al., Int. Rev. ImmunoL—13(1):65-93 (1995).
Muller, B., et al., Eur. J. ImmunoL—22(6): 1621-1625 (1992).
Muller, R., et al., PNAS—97(15): 8451-8454 (2000).
Neuberger, M.S., et al., Nature—338:350-352 (1989).
Pelanda, R., et al., Journal of Immunology—169:865-872 (2002).
Pike, K.A., et al., Journal of Immunology—172:2210-2218 (2004).
Pluschke, G., et al, Journal of Immunological Methods—215:27-37 (1998).
Reichlin, A., et al, Journal of Experimental Medicine—193(1):13-23 (2001).
Reth, M., Annu. Rev. ImmunoL—10:97-121 (1992).
Riechmann, L., et al., Nature—332:323-327 (1988).
Sayegh, C.E., et al., Immunological Reviews—175:187-200 (2000).
Schamel, et al., PNAS—100(17): 9861-9866 (2003).
Skolnick et al., Trends in Biotech, vol. 18, p. 34-39, (2000).
Tomasinsig et al., Current Protein and Peptide Science, vol. 6, p. 23-34, (2005).
Venkitaraman, A.R., et al., Nature—352:777-781 (1991).
Verhoeyen, M., et al., Science—239:1534-1536 (1988).
Vuillier, F., et al., Blood, 105(7): 2933-2940 (2005)).
Wakayama, T., et al., Nature—394:369-374 (1998).
Wang, H., et al, J. Immunology—171:6381-6388 (2003).
Wienands, J., et al., EMBO J.—9(2):449-455 (1990).
Jianglin Fan, et al., "Transgenic rabbit models for biomedical research: Current status, basic methods and future perspectives", *Pathology International* 1999: 49: 583-594.

\* cited by examiner

Figure 1: Ig alpha

```
                                        10        20        30        40        50        60        70
                                  ....|....|....|....|....|....|....|....|....|....|....|....|....|....|
human M74721                              A    A              AVY       A   HKV A  M       AHF  P  S  NA---
bos D16412                        E  QA   P  .       -    .AG      .    W               V    T  G  T----
mouse NM_007655                   .  LEA  .  LL    ---- YAC       .  R  G              .  T  E  GR P----
canis XM_541597 predicted                 .  C. T         .GG    S  .   G              T.    L  R  RL SKL
pan XM_512693 predicted           S       .  .            .A.         .   ... .  .        ...   .  .  ..---
rabbit predicted                  ------------------------------------------------------------------------

80        90       100       110       120       130       140
                                  ....|....|....|....|....|....|....|....|....|....|....|....|....|....|
human M74721                         H    Y      E     D  T     N      G  V         Y-----            ------
bos D16412                        H  S  S       MYRGDV AG       P      R  R   S  -  KI-----            ------
mouse NM_007655                   FS S  I        P     TT       FFPE   R  W   I  N-NIL-----            ------
canis XM_541597 predicted            A  D  SY          T DT     M      R     K  L  QKILSS             ------
pan XM_512693 predicted           .  .     .       .   .    .   .      .     .-----                   REWPSP
rabbit predicted                  ------------------------------------------------------------------------

150       160       170       180       190       200       210
                                  ....|....|....|....|....|....|....|....|....|....|....|....|....|....|
human M74721                      -----------------------------------------       P                A
bos D16412                        -----------------------------------------                 N  .    .I
mouse NM_007655                   ----------------------------------------N
canis XM_541597 predicted         -----------------------------------------       R             N  .
pan XM_512693 predicted           GPYSHCPAGDTRFIPEVGIEPIPSMWVSNRLGQRDGHSPLQ                          .
rabbit predicted                  ------------------------------------------------------------------------

220       230       240       250       260       270       280
                                  ....|....|....|....|....|....|....|....|....|....|....|....|....|....|
human M74721                      A              ---------------------            L    AG
bos D16412                        .              ---------------------            M    A  IQ
mouse NM_007655                   .              ---------------------                 MP
canis XM_541597 predicted         .              ---------------------            M    .Q
pan XM_512693 predicted           .              VSPLGPLSQPGEGLGRGTPNAQ            .    .  .
rabbit predicted                  ------------------------------------------------------------------------

290       300
                                  ....|....|....|....|
human M74721                                    --            (SEQ ID NO. 1)
bos D16412                                      --A           (SEQ ID NO. 2)
mouse NM_007655                                 --A           (SEQ ID NO. 3)
canis XM_541597 predicted                       GD            (SEQ ID NO. 4)
pan XM_512693 predicted                         --            (SEQ ID NO. 5)
rabbit predicted                       D        --            (SEQ ID NO. 6)
```

Figure 2: Ig beta

```
                                        10         20         30         40         50         60         70
                                   ....|....|....|....|....|....|....|....|....|....|....|....|....|....|
human M80461                       AR A      S      A      A    AA      Y      A      S      A    RF       M SA
canis XP_850416 predicted           .g        h             --  ..      h      t g            .    ga     r kd-
rattus BAA25652                     .t        c      f          .m ks ppif      p             a.                y-
bos XP_586841 predicted             .gs. i gln       g          k l.d   ll      t             .    g      r v d-
mus AAH12226                        .t        s c    f    f     .m   s lpl f    p             a.                h-
gallus CAG31473                     --- gdfcrrlwv q n w a.aaggip dg sts rt   e vg       .a         h i         q-

80         90        100        110        120        130        140
                                   ....|....|....|....|....|....|....|....|....|....|....|....|....|....|
human M80461                        N    LW    M N     KL      E    E A       G             -NTSE  YQ
canis XP_850416 predicted           v a  ...    . l    p pr  -      d  .      . s           --s gsf  k
rattus BAA25652                     v         nq -     fp    h s      g y                   t pd
bos XP_586841 predicted             d l      p p s     t ha      h k e.v  1                 akg.qrteh
mus AAH12226                        a         -s       vs             g y                     anhn   s
gallus CAG31473                     pha q  -al ng    fhv dqssd fsi ntndri f  sr s      v ds nl e krqp s 150        160        170        180        190        200        210
                                   ....|....|....|....|....|....|....|....|....|....|....|....|....|....|
human M80461                                  A                                     A                 A
canis XP_850416 predicted                     .                                     .                 .
rattus BAA25652                     l         d                                     .                 .
bos XP_586841 predicted                       .                                     .                 .
mus AAH12226                        l         d                                   g .                 .
gallus CAG31473                         sr n q    n         t            s   l f  g r erp           i.

220        230
                                   ....|....|....|....|
human M80461                                             (SEQ ID NO. 7)
canis XP_850416 predicted                                (SEQ ID NO. 8)
rattus BAA25652                                          (SEQ ID NO. 9)
bos XP_586841 predicted                                  (SEQ ID NO. 10)
mus AAH12226                                             (SEQ ID NO. 11)
gallus CAG31473                      tpf dm a            (SEQ ID NO. 12)
```

ENHANCED EXPRESSION OF HUMAN OR HUMANIZED IMMUNOGLOBULIN IN NON-HUMAN TRANSGENIC ANIMALS

CROSS-REFERENCE TO RELATED APPLICATIONS

This application is a continuation application of U.S. patent application Ser. No. 11/895,910, filed Aug. 27, 2007, now abandoned which claims priority under 35 U.S.C. Section 119(e) and the benefit of U.S. Provisional Application Ser. No. 60/841,980, filed on Sep. 1, 2006, the contents of which are incorporated herein by reference in their entireties.

FIELD OF THE INVENTION

This invention relates to a method to improve the expression of human(ized) immunoglobulin in non-human transgenic animals by promoting normal B-cell development and by sustaining the expression of human(ized) antibodies in non-human animals harboring human(ized) immunoglobulin loci. In particular, this invention relates to the simultaneous expression of transgenes encoding human(ized) Igα and/or Igβ, components of the B-cell receptor, and transgenes encoding a human(ized) immunoglobulin locus or loci. This method allows for the dominant expression of human(ized) antibodies, for example in the blood, milk or eggs of the transgenic non-human animals.

DESCRIPTION OF THE RELATED ART

Antibodies are an important class of pharmaceutical products that have been successfully used in the treatment of various human diseases and conditions, such as cancer, allergic diseases, prevention of transplant rejection and host-versus-graft disease.

A major problem of the antibody preparations obtained from non-human animals is the intrinsic immunogenicity of non-human immunoglobulins in human patients. In order to reduce the immunogenicity of non-human antibodies, it has been shown that by fusing animal variable (V) region exons with human constant (C) region exons, a chimeric antibody gene can be obtained. Such chimeric or humanized antibodies have minimal immunogenicity to humans and are appropriate for use in the therapeutic treatment of human subjects.

Humanized monoclonal antibodies have been developed and are in clinical use. However, the use of monoclonal antibodies in general, whether chimeric, humanized or human, for the treatment of devastating diseases such as cancer or infections with virulent pathogens, is limited due to the complexity, multifactorial etiology and adaptivity of these diseases. Monoclonal antibodies directed against singularly defined targets usually fail when those targets change, evolve and mutate. For instance, malignancies may gain resistance to standard monoclonal antibody therapies. A solution to this problem is to use polyclonal antibodies which have the ability to target a plurality of evolving targets. Polyclonal antibodies can neutralize bacterial or viral toxins, and direct immune responses to kill and eliminate pathogens.

Accordingly, there is a great clinical need for suitable methods for the large-scale production of high-titer, high-affinity, humanized polyclonal and monoclonal antibodies. Further, since production of antibodies in larger transgenic animals like rabbits, chickens, sheep and cows is favored from the standpoint of antibody yield, creation of larger founder animals expressing higher amounts of transgene-encoded products is also highly desirable.

Humanized monoclonal antibodies are typically human antibodies in which some CDR residues, and possibly some FR residues, are substituted by residues from analogous sites in non-human, animal, e.g. rodent, antibodies. Humanization can be essentially performed following the method of Winter and co-workers (Jones et al., *Nature,* 321: 522 (1986); Riechmann et al., *Nature,* 332: 323 (1988); Verhoeyen et al., *Science,* 239: 1534 (1988)), by substituting non-human, animal CDRs or CDR sequences (e.g. rodent), for the corresponding sequences of a human monoclonal antibody.

While making humanized antibodies in animals, one problem encountered is the endogenous production of host antibody over transgenic antibody, which needs to be suppressed. It has been described that the homozygous deletion of the antibody, heavy-chain joining region (JH) gene in chimeric and germ-line mutant mice, results in the complete inhibition of endogenous antibody production. Transfer of a human germ-line immunoglobulin gene array into such germ-line mutant mice will result in the production of human antibodies upon antigen challenge. See, e.g., Jakobovits et al., *Proc. Natl. Acad. Sci USA,* 90: 2551 (1993); Jakobovits et al., *Nature,* 362: 255 (1993); Bruggemann et al., *Year in Immunol.,* 7: 33 (1993); U.S. Pat. No. 7,064,244 issued Jun. 20, 2006; the disclosures of which are incorporated herein by reference in their entirety.

The introduction of human immunoglobulin genes into the genome of mice results in the expression of a diversified human antibody repertoire in these genetically engineered mice. The generation of mice expressing human-mouse chimeric antibodies has been described by Pluschke et al., *Journal of Immunological Methods* 215: 27-37 (1998). The generation of mice expressing human immunoglobulin polypeptides has been described by Neuberger et al., *Nature* 338: 350-2 (1989); Lonberg et al., *Int. Rev. Immunol.* 13(1):65-93 (1995); and Bruggemann et al., *Curr. Opin. Biotechnol.,* 8(4): 455-8 (1997); U.S. Pat. No. 5,545,806, issued August 1996; U.S. Pat. No. 5,545,807, issued August 1996 and U.S. Pat. No. 5,569,825, issued October 1996; the disclosures of which are incorporated herein by reference in their entirety. The generation of cows expressing human antibodies has been described by Kuroiwa et al., *Nature Biotech* 20(9): 889-894 (2002). The production of non-human transgenic animals expressing human(ized) immunoglobulin transloci and the production of antibodies from such transgenic animals have also been described in detail in PCT Publication Nos. WO 92/03918, WO 02/12437, and in U.S. Pat. Nos. 5,814,318, and 5,570,429, the disclosures of which are hereby expressly incorporated by reference in their entirety. The humanized antibodies obtained have minimal immunogenicity to humans and are appropriate for use in the therapeutic treatment of human subjects.

While the genetic engineering approaches cited above result in the expression of human immunoglobulin polypeptides in genetically engineered mice, the level of human immunoglobulin expression is lower than normal. This may be due to species-specific regulatory elements in the immunoglobulin loci that are necessary for efficient expression of immunoglobulins. As demonstrated in transfected cell lines, regulatory elements present in human immunoglobulin genes may not function properly in non-human animals. Several regulatory elements in immunoglobulin genes have been described. Of particular importance are enhancers downstream (3') of heavy chain constant regions and intronic enhancers in light chain genes. In addition, other, yet to be identified, control elements may be present in immunoglobulin genes. Studies in mice have shown that the membrane and cytoplasmic tail of the membrane form of immunoglobulin molecules play an important role in expression levels of human-mouse chimeric antibodies in the serum of mice homozygous for the human Cγ1 gene. Therefore, for the expression of heterologous immunoglobulin genes in animals, it is desirable to replace sequences that contain enhancer elements and exons encoding transmembrane (M1 exon) and cytoplasmic tail (M2 exon) with sequences that are normally found in the animal in similar positions.

Human immunoglobulin expression in these genetically engineered animals may also be affected by B-cell development of the non-human B-cells carrying the human or humanized immunoglobulin loci. The influence of the B-cell receptor (BCR) on B-cell development has been studied extensively in mice. However, it has been unclear how a human or partially human antibody combines to form a functional BCR, and whether such a BCR would efficiently influence the development and survival of non-human B-cells expressing human(ized) Ig, in transgenic animals, which, in turn, would affect antibody yields.

BRIEF DESCRIPTION OF DRAWINGS

FIG. 1 shows an amino acid alignment of the human Igα polypeptide sequence (SEQ ID NO: 1) with other non-human Igα sequences (SEQ ID NOs: 2-6).

FIG. 2 shows an amino acid alignment of the human Igβ polypeptide sequence (SEQ ID NO: 7) with other non-human Igβ sequences (SEQ ID NOs: 8-12).

SUMMARY OF THE INVENTION

In one aspect, the invention provides a transgene construct encoding a chimeric Igα subunit of the BCR, wherein the chimeric Igα subunit comprises an intracellular domain sequence and a transmembrane domain sequence of a non-human, Igα polypeptide sequence; and further, a polypeptide having at least 85% sequence identity to the extracellular domain of human Igα of SEQ ID NO.: 1.

In a second aspect, the invention provides a transgene construct encoding a chimeric Igβ subunit of the BCR, wherein the chimeric Igβ subunit comprises an intracellular domain sequence and a transmembrane domain sequence of a non-human, Igβ polypeptide sequence, and further, a polypeptide having at least 85% sequence identity to the extracellular domain of the human Igβ of SEQ ID NO.: 7.

In a certain embodiment of the invention, the type of non-human Igα polypeptide sequence includes, but is not limited to, the bovine (SEQ ID NO: 2); murine (SEQ ID NO: 3); canine (SEQ ID NO: 4); primate ((SEQ ID NO: 5); rabbit (SEQ ID NO: 6) or other non-human sequences. In another embodiment of the invention, the type of non-human IV polypeptide sequence includes, but is not limited to, the canine (SEQ ID NO: 8); rat (SEQ ID NO: 9); bovine (SEQ ID NO: 10); murine (SEQ ID NO: 11); chicken (SEQ ID NO: 12) or other non-human sequences.

In a third aspect, the non-human transgenic animal comprises (a) a transgene construct encoding either a full-length, human Igα subunit of SEQ ID NO.: 1, or the chimeric Igα subunit as defined above, and/or, (b) a transgene construct encoding either a full-length, human Igβ subunit of SEQ ID NO.: 7, or the chimeric Igβ subunit, as defined above, and, (c) a transgene construct encoding a human(ized) immunoglobulin locus, wherein the resultant transgene products combine to form a human(ized) B-cell receptor complex.

In one embodiment of this aspect, the expression of any endogenous Ig production, and/or, endogenous Igα and/or endogenous Igβ subunit expression, of the non-human transgenic animal is substantially reduced.

In another embodiment, the non-human transgenic animal is selected from a group consisting of rabbit, mouse, rat, pig, sheep, goat, bird, horse, donkey and cow. In a preferred embodiment, the non-human transgenic animal is a rabbit.

In a fourth aspect, the invention also provides an isolated human(ized) immunoglobulin from the non-human transgenic animal defined above, which is either an antibody or an antibody fragment. In a certain embodiment of this aspect, the isolated human(ized) immunoglobulin is either a polyclonal or a monoclonal antibody, or alternately, is an antibody fragment. The antibody fragment can be either from a polyclonal or a monoclonal antibody. Further, the antibody or the antibody fragment can be labeled, or fused to a toxin to form an immunotoxin, or coupled to a therapeutic agent, or fused to any heterologous amino acid sequence well-defined and used in the art. In some embodiments, the antibody fragment is a Fc, Fv, Fab, Fab' or F(ab')$_2$ fragment.

In a fifth aspect, the invention provides an isolated B-cell from the non-human transgenic animal defined above, where the B-cell expresses either the native human Igα subunit or a chimeric Igα subunit and/or either the native human Igβ subunit or the chimeric Igβ subunit, and further, also expresses the human(ized) immunoglobulin locus. In certain embodiments, this B-cell is immortalized and in a preferred embodiment, is derived from a rabbit.

In a sixth aspect, the invention provides an antibody preparation comprising an antibody or an antibody fragment, as described above.

In a seventh aspect, the invention provides a pharmaceutical composition comprising an antibody or antibody fragment, as described above, in a mixture with a pharmaceutically acceptable ingredient. The pharmaceutical composition can comprise either a monoclonal antibody or a fragment thereof, or, one or a plurality of polyclonal antibodies or fragments thereof.

In an eighth aspect, the invention provides a method for producing human(ized) antibodies in a non-human animal comprising: (a) introducing and expressing a transgene construct encoding either a native human Igα subunit or a chimeric Igα subunit, and/or a transgene construct encoding either a native human IgΔ subunit or a chimeric Igβ subunit into the non-human animal; and, (b) introducing and expressing a transgene construct encoding a human(ized) immunoglobulin locus into the non-human animal; (c) subjecting the animal to an antigenic stimulus; and (d) isolating human(ized) antibodies from the animal. In a certain embodiment of this aspect, the antibody is either a polyclonal or a monoclonal antibody, or is a fragment of a polyclonal or a monoclonal antibody. Further, the antibody or antibody fragment can either be labeled, or can be fused to a toxin to form an immunotoxin, or coupled to a therapeutic agent, or can be fused to any heterologous amino acid sequence.

In a ninth aspect, the invention provides a method for producing a non-human animal expressing human(ized) antibodies comprising: (a) introducing and expressing a transgene construct encoding either a native human Igα subunit or a chimeric Igα subunit and/or a transgene construct encoding either a native human Igβ subunit or a chimeric Igβ subunit into the B-cell of the non-human animal; and, (b) introducing and expressing a transgene construct encoding a human(ized) immunoglobulin locus into the non-human animal; wherein the resultant transgene products combine to form a human(ized) B-cell receptor complex. In one embodiment, the non-human animal expressing human(ized) antibodies is an animal that creates antibody diversity by gene conversion and/or somatic hypermutation. In a preferred embodiment, the animal is a rabbit.

DETAILED DESCRIPTION OF THE INVENTION

Definitions

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), and March, *Advanced Organic. Chemistry Reactions, Mechanisms and Structure* 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"A transgene construct or expression construct" as defined herein, refers to a DNA molecule which contains the coding sequence for at least one transgene of interest along with appropriate regulatory sequences required for temporal, cell specific and/or enhanced expression of the transgene(s) of interest within target cells of a non-human transgenic animal.

"B-cells" are defined as B-lineage cells that are capable of undergoing rearrangement of immunoglobulin gene segments and expressing immunoglobulin genes at some stage in their life cycle. These cells include, but are not limited to, early pro-B-cells, late pro-B-cells, large pre-B-cells, small pre-B-cells, immature B-cells, mature B-cells, memory B-cells, plasma cells, etc.

"B-cell receptor (BCR) complex" as defined herein, refers to the multisubunit immune recognition receptor expressed on B-cells, which includes the following subunits: the antigen (Ag) receptor, the membrane-bound immunoglobulin (mIg), the Igα subunit and the Igβ subunit. The B-cell receptor, its components, and its association with the five immunoglobulin classes have been described by Wienands et al., *EMBO J.* 9(2): 449-455 (1990), Venkitaraman et al., *Nature* 352: 777-781 (1991), Herren et al., *Immunologic Res.* 26(1-3): 35-43 (2002). In addition, there are several BCR-associated proteins (BAPs) that have been cloned and sequenced, but their function(s) remain unknown, and their role, as components of the BCR, has been questioned. BCR-associated proteins have been described by Adachi et al., *EMBO J* 15(7): 1534-1541 (1996) and Schamel et al., *PNAS* 100(17): 9861-9866 (2003).

"Native Igα or Igβ subunits" refer to naturally occurring Igα or Igβ polypeptide sequences, which include naturally occurring alleles of Igα or Igβ subunits found in a given type of animal, or in a related species. These are also referred to as "full-length Igα or Igβ sequences". The human Igα polypeptide sequence was cloned by Flaswinkel et al., *Immunogenetics* 36 (4): 266-69 (1992); Accession number M74721 (FIG. 1, SEQ ID NO: 1). The human Igβ polypeptide sequence was cloned by Mueller et al., *Eur. J. Biochem.* 22, 1621-25 (1992); Accession number M80461 (FIG. 2, SEQ ID NO: 7).

The term "human(ized)" refers to an entirely human sequence or a sequence containing one or more human sequences. Thus, the term, as used herein, includes human and humanized sequences.

A "chimeric Igα" subunit or protein or polypeptide refers to an Igα polypeptide sequence from an animal (e.g.; rat, mouse, human, rabbit, chicken, etc.), in which one or more domains of the Igα polypeptide are replaced with a corresponding domain or domains from a different Igα polypeptide of another animal or species, or with a corresponding domain or domains from a different allelic Igα version, or from a variant Igα sequence with one or more amino acid substitutions, or from a variant Igα sequence having at least 85% sequence identity to the corresponding domain of a given Igα sequence. The terms "chimeric Igα" and "human (ized) Igα" are used interchangeably throughout the specification. Igα polypeptide sequences (SEQ ID NOs: 2-6) from some non-human animals are also defined in FIG. 1.

A "chimeric Igβ" subunit or protein or polypeptide refers to an Igβ polypeptide sequence from an animal (e.g.; rat, mouse, human, rabbit, chicken, etc.), in which one or more domains of the Igβ polypeptide are replaced with a corresponding domain or domains from a different Igβ polypeptide of another animal or species, or with a corresponding domain or domains from a different allelic Igβ version, or from a variant Igβ sequence with one or more amino acid substitutions, or from a variant Igβ sequence having at least 85% sequence identity to the corresponding domain of a given Igβ sequence. The terms "chimeric Igβ" and "human (ized) Igβ" are used interchangeably throughout the specification. Igβ polypeptide sequences (SEQ ID NOs: 8-12) from some non-human animals are defined in FIG. 2.

"Intracellular polypeptide or domain" or "cytoplasmic tail" refers to that part of the polypeptide sequence of a given membrane-bound protein or subunit that exists within the bounds of the cell. Usually, the intracellular domain of the protein is responsible for signal transduction.

By "intracellular domain sequence" of an Igα or Igβ subunit is meant the polypeptide sequence of the Igα or Igβ polypeptide, or fragments thereof, that usually exist within the bounds of the cell.

"Transmembrane domain sequence" of an Igα or Igβ subunit is meant the polypeptide sequence of the Igα or Igβ polypeptide, or fragments thereof that spans a biological membrane such as a plasma membrane, organelle membrane, or lipid bilayer. The "transmembrane domain sequence" as defined herein includes naturally occurring membrane-spanning polypeptides, or can be non-naturally occurring consensus sequences, or fragments thereof.

"Extracellular polypeptide or domain" refers to that part of the polypeptide sequence of a given membrane-bound protein or subunit that usually exists outside the bounds of the cell. By "extracellular domain of Igα or Igβ" is meant the polypeptide sequence of the Igα or Igβ polypeptide, or fragments thereof, that exist outside the bounds of the cell.

The term "human(ized) immunoglobulin locus" as used herein includes both naturally occurring sequences of a human immunoglobulin or Ig gene locus or a segment thereof, degenerate forms of naturally occurring sequences of a human Ig gene locus or segments thereof, as well as synthetic sequences that encode a polypeptide sequence substantially identical to a polypeptide encoded by a naturally occurring sequence of a human Ig gene locus or a segment thereof. In a particular embodiment, the human Ig gene segment renders the immunoglobulin molecule non-immunogenic in humans. Here, the terms "human(ized) or humanized immunoglobulin (Ig) heavy and/or light chain locus" or "human or human(ized) immunoglobulin or Ig locus" are used interchangeably.

The term "human(ized) B-cell receptor (BCR) complex" as used herein refers to those multisubunit BCR complexes in which the Igα subunit is either a native, human Igα subunit or a chimeric Igα subunit having human or humanized Igα sequences as described above; and/or further, in which the Igβ subunit is either a native, human Igβ subunit or a chimeric Igβ subunit having human or humanized Igβ sequences as described above; and further, where the membrane-bound immunoglobulin (mIg) is that of a human(ized) immunoglobulin, as described above.

The terms "human antibody" and "human immunoglobulin" are used herein to refer to antibodies and immunoglobulin molecules comprising fully human sequences.

The terms "humanized antibody" and "humanized immunoglobulin," as used herein, mean an immunoglobulin molecule comprising at least a portion of a human immunoglobulin polypeptide sequence (or a polypeptide sequence encoded by a human immunoglobulin gene segment). The humanized immunoglobulin molecules of the present invention can be isolated from a transgenic non-human animal engineered to produce humanized immunoglobulin molecules. Such humanized immunoglobulin molecules are less immunogenic to primates, especially humans, relative to non-humanized immunoglobulin molecules prepared from the animal or prepared from cells derived from the animal. Humanized immunoglobulins or antibodies include immunoglobulins (Igs) and antibodies that are further diversified through gene conversion and somatic hypermutations in gene converting animals. Such humanized Ig or antibodies are not "human" since they are not naturally made by humans (since humans do not diversify their antibody repertoire through gene conversion) and yet, the humanized Ig or antibodies are not immunogenic to humans since they have human Ig sequences in their structure.

By the term "substantially reduced" endogenous Ig production, and/or Igα and/or Igβ subunits expression is meant that the degree of production of either the endogenous Ig alone or additionally, endogeous Igα and/or Igβ expression is reduced preferably at least about 30%-49%, or more preferably at least about 50%-79%, or even more preferably at least about 80%-89%, or most preferably by about 90-100% in the transgenic animal.

The term "monoclonal antibody" is used to refer to an antibody molecule synthesized by a single clone of B-cells.

The term "polyclonal antibody" is used to refer to a population of antibody molecules synthesized by a population of B-cells.

An "immunoglobulin (Ig) locus" having the capacity to undergo gene rearrangement and gene conversion is also referred to herein as a "functional" Ig locus, and the antibodies with a diversity generated by a functional Ig locus are also referred to herein as "functional" antibodies or a "functional" repertoire of antibodies.

The term "non-human (transgenic) animal" as used herein includes, but is not limited to, mammals such as, for example, non-human primates, rodents (e.g. mice and rats), non-rodent mammals, such as, for example, rabbits, pigs, sheep, goats, cows, pigs, horses and donkeys, and birds (e.g., chickens, turkeys, ducks, geese and the like). The term "non-primate animal" as used herein includes, but is not limited to, mammals other than primates, including but not limited to the mammals specifically listed above.

DETAILED DESCRIPTION

This invention is based, at least in part, on the recognition that the production of human or humanized immunoglobulin (including immunoglobulin chains) in a non-human transgenic animal can be significantly increased by co-expressing human or humanized Igα and/or Igβ in the B cells of the animal. The inclusion of human or humanized Igα and/or Igβ in the B cells in transgenic animals is believed to reconstitute and improve interactions between the B-cell receptor proteins, thereby enhancing antigen recognition, B-cell development and survival of the B cells carrying such transgenes. The co-expression of humanized immunoglobulin in transgenic animals already carrying the human or humanized Igα and/or IGβ transgenes would vastly improve humanized immunoglobulin production. It would be additionally desirable to express both, the human or humanized Igα and/or Igβ transgene and the humanized immunoglobulin transgene against a knockout background of, preferably, both endogenous Ig, as well as endogenous Igα and/or Igβ.

The B-Cell Receptor and its Associated Proteins

The B-cell receptor consists of membrane bound immunoglobulin and a signal-transducing heterodimer, consisting of two disulfide-linked glyoproteins called Igα and Igβ. In addition, BCR associated proteins (BAPs) have been described.

Expression of the BCR is important for B-cell development, selection and survival. These processes depend on BCR signaling through the Igα/Igβ heterodimer. The cytoplasmic domains of these molecules carry a sequence motif that contains several tyrosine residues assembled into the so-called immunoreceptor tyrosine-based activation motif (ITAM), which are phosphorylated upon BCR triggering.

Gene targeting experiments have shown that the cytoplasmic domains of the Igα/Igβ heterodimer are crucial for B-cell development. Signals transduced by the Igα/Igβ heterodimer are involved in both positive and negative selection of developing B-cells.

A membrane bound immunoglobulin (mIg) molecule consists of two heavy chains, forming a homodimer, and two light chains, each of which is covalently bound to one of the heavy chains. At the N-terminus the heavy chain carries a VH domain, which, depending on the isotype, is followed by either 4 (IgM, IgE), 3 (IgG, IgA) or 2 (IgD) C-domains. The antigen-binding site is formed by the hypervariable regions of a VH:VL pair. Thus, each mIg molecule has two antigen binding sites.

The mIgM molecule differs from the secreted form of IgM in that the secreted IgM forms a pentamer with 10 potential antigen binding sites. The pentamerization is controlled by sequences in the C-terminal part of the secreted μs chain. This part, consisting of 22 amino acids, is absent in the membrane-bound μm chain, which instead carries 48 C-terminal amino acids encoded by the M1 and M2 exons.

The μm-specific part of the sequence is the most evolutionarily conserved part of the whole IgM molecule. It is nearly identical between mouse, rabbit and human mIgM, and the conservation is still obvious if one compares mouse with shark mIgM. Conservation of amino acids is also apparent when one compares the C-terminal sequence of mIgM to that of other mIg isotypes of the mouse. This finding provides evidence that the conserved transmembrane amino acids are interacting either with each other in the H chain homodimer or with the Igα and Igβ subunits.

Both, Igα and Igβ have a 22 amino acid transmembrane segment, followed by a C-terminal cytoplasmic tail of about 40-70 amino acids, which contain several tyrosine residues.

At the N-terminus, both proteins carry a leader peptide, followed by a extracellular domain containing cysteine residues, a tryptophan, as well as several other conserved amino acids found in proteins of the Ig superfamily. This suggests that the extracellular parts of both Igα and Igβ subunits form an Ig-like domain. Besides cysteines that form intra-domain disulfide bonds, the Igα and Igβ sequences contain additional cysteines that presumably form inter-chain disulfide bonds between the Igα and Igβ subunits.

A comparison between the mouse and the human Igα sequence shows that, all residues important for the information of the Ig domain and inter-chain bonds are conserved between the Igα of the two species. The comparison, however, also shows that sequence conservation in the extracellular part only amounts to about 56%, while the transmembrane and cytoplasmic tail show conservation of 100% and 87%, respectively. The latter reflects the importance of the residues within the C-terminal part of the molecule.

The assembly of the mIgM molecule with the Igα/Igβ heterodimer is necessary for surface expression of mIgM. This requirement can be abolished by mutations of the transmembrane part of the μm chain. For example, replacement of the transmembrane region of the μm chain with the transmembrane part of the H-2K$^K$ molecule results in the surface expression of mIgM independent of Igα/Igβ. These data demonstrate that the μm transmembrane region is required for specific interactions between the μm chain and the Igα/Igβ heterodimer. In addition, B-cells have a control mechanism that prevents transport of single or incompletely assembled components of transmembrane protein complex out of the ER.

Although the transmembrane portions of the BCR are probably the most important structures that are required for the formation of the BCR complex, the extracellular Ig-domain of Igα and Igβ has also been suggested to play a role in the binding of the mIgM molecule. For instance, in the mouse cell line J558Lμm, which does not express mouse Igα, transfection with an Igα transgene restored the surface expression of mIgM. Interestingly, transfection with a mouse Igα gene resulted in 10-times higher expression than transfection with a human Igα gene. This data suggests that the extracellular domain of Igα, additionally, may interact with the extracellular parts of mIgM. On the other hand, transgenic mice with human immunoglobulin loci do express human immunoglobulins. It remains unclear whether B-cell development, B-cell survival or expression of human(ized) mIgM in transgenic non-human animals would be influenced by the co-expression of human Igα and/or human Igβ in B-cells carrying human(ized) mIgM genes.

In addition, there are several BCR-associated proteins (BAPs) that have been cloned and sequenced, but their function(s) remain unknown. Even though these proteins are associated with the BCR, their role, as components of the BCR, has been questioned. Yet, the ubiquitous expression and strong evolutionary conservation of BAPs suggest that they must play an important role, possibly in general cellular processes and several putative functions have been proposed. For example, these proteins may be involved in coupling the BCR to the cytoskeleton, or in controlling vesicular transport. Lastly, it has been proposed that they function as chaperones, helping in the folding and assembly of transmembrane proteins.

Relevant Literature

The B-cell receptor, its components, and its association with the five immunoglobulin classes have been described by Wienands et al., *EMBO J.* 9(2): 449-455 (1990), Venkitaraman et al., *Nature* 352: 777-781 (1991), Herren et al., *Immunologic Res.* 26(1-3): 35-43 (2002). BCR associated proteins have been described by Adachi et al., *EMBO J* 15(7): 1534-1541 (1996) and Schamel et al., *PNAS* 100(17): 9861-9866 (2003). The influence of the B-cell receptor on B-cell development and survival has been described by Reth, *Annual Reviews of Immunology* 10: 97-121 (1992), Kraus et al., *Cell* 117(6): 787-800 (2004), Sayegh et al., *Immunological Reviews* 175: 187-200 (2000), Reichlin et al, *Journal of Experimental Medicine* 193(1): 13-23 (2001), Pike et al., *Journal of Immunology* 172: 2210-2218 (2004), Pelanda et al., *Journal of Immunology* 169: 865-872 (2002). Regulation of BCR signaling and its influence in B-cell development and apoptosis have been described in Cronin et al., *J. Immunology* 161: 252-259 (1998), Muller et al., *PNAS* 97 (15): 8451-8454 (2000), Cragg et al., *Blood* 100: 3068-3076 (2002), Wang et al., *J. Immunology* 171: 6381-6388 (2003), Fuentes-Pananá et al., *J. Immunology* 174: 1245-1252 (2005). The disclosures of the above cited references are incorporated herein by reference in their entirety.

The present invention therefore is directed to methods for co-expressing human(ized) Igα and/or human(ized) Igβ in B-cells, particularly in transgenic animals that are capable of producing a diversified human(ized) antibody repertoireto improve B-cell survival in such transgenic animals. Types of animals include larger non-human animals like rabbits, birds, chickens, sheep, goats, cows, swine, horses and donkeys. When these animals express an Ig translocus, because of their larger size, their antibody yields should also be greater. Thus, this invention aims at creating larger founder animals producing higher amounts human(ized) immunoglobulins through enhanced B-cell development and survival.

Accordingly, the present invention is directed to transgene constructs encoding full-length human Igα and Igβ polypeptides, or, chimeric transgene constructs encoding for chimeric or humanized Igα and chimeric or humanized Igβ polypeptides, as defined further below.

By "transgene or transgene construct encoding the human Igα and/or Igβ polypeptide" is meant the native, full length, human Igα and/or Igβ DNA sequence respectively, as well as any variant, codon optimized DNA sequence which encodes for a functionally equivalent polypeptide of Igα or Igβ, but which has a different DNA sequence based on codon degeneracy. This concept is discussed in detail further below. The native, full length, human Igα polypeptide sequence is defined in SEQ ID NO: 1 (FIG. 1). The native, full length, human Igβ polypeptide sequence is defined in SEQ ID NO: 7 (FIG. 1).

Also referred to herein is "nucleic acid molecule or transgene or transgene construct encoding the chimeric or human(ized) Igα". A "chimeric Igα" subunit or protein or polypeptide refers to an Igα polypeptide sequence from an animal (e.g.; rat, mouse, human, rabbit, chicken, etc.), in which one or more domains of the Igα polypeptide are replaced with a corresponding domain or domains from a different Igα polypeptide of another animal or species, or with a corresponding domain or domains from a different allelic Igα version, or from a variant Igα sequence with one or more amino acid substitutions, or from a variant Igα sequence having at least 85% sequence identity to the corresponding domain of a given Igα sequence. The terms "chimeric Igα" and "human(ized) Igα" are used interchangeably throughout the specification. The non-human Igα polypeptide sequences from which the intracellular and/or the transmembrane domain sequences can be obtained, for example, include, but are not limited to, bovine (SEQ ID NO: 2); murine (SEQ ID NO: 3); canine (SEQ ID NO: 4); primate ((SEQ ID NO: 5); rabbit (SEQ ID NO: 6) or other non-human sequences.

Also referred to herein is "nucleic acid molecule or transgene or transgene construct encoding the chimeric or human(ized) Igβ". A "chimeric Igβ" subunit or protein or polypeptide refers to an Igβ polypeptide sequence from an animal (e.g.; rat, mouse, human, rabbit, chicken, etc.), in which one or more domains of the Igβ polypeptide are replaced with a corresponding domain or domains from a different Igβ polypeptide of another animal or species, or with a corresponding domain or domains from a different allelic Igβ version, or from a variant Igβ sequence with one or more amino acid substitutions, or from a variant Igβ sequence having at least 85% sequence identity to the corresponding domain of a given Igβ sequence. The terms "chimeric Igβ" and "human(ized) Igβ" are used interchangeably throughout the specification. The non-human Igβ polypeptide sequences from which the intracellular and/or the transmembrane domain sequences can be obtained, for example, include, but are not limited to, canine (SEQ ID NO: 8); rat (SEQ ID NO: 9); bovine (SEQ ID NO: 10); murine (SEQ ID NO: 11); chicken (SEQ. ID NO: 12); or other non-human sequences.

Thus, briefly, a chimeric Igα or Igβ transgene consists of 1) a nucleotide sequence encoding the extracellular domain of the human Igα or Igβ respectively, and 2) a nucleotide sequence encoding the transmembrane and the intracellular domain of the Igα or Igβ from the host transgenic animal, respectively.

In a further aspect, the present invention is also directed to transgenic constructs encoding for a human(ized) immunoglobulins or locii as described in a previously filed U.S. applications, now available as U.S. Publication No. 2003-0017534, published Jan. 23, 2003 and U.S. Publication No. 2006-0026696, published Feb. 2, 2006, the disclosures of which is hereby incorporated by reference in their entirety. The transgenic animals, B-cells or cell lines generated thereof, and the relevant methodologies disclosed therein also form an aspect of this invention.

In an alternative approach to the above mentioned aspect, the present invention is also directed to transgenic constructs encoding for human(ized) immunoglobulin or Ig chain or loci, as described in U.S. Pat. No. 5,545,806, issued August 1996; U.S. Pat. No. 5,545,807, issued August 1996 and U.S. Pat. No. 5,569,825, issued October 1996, U.S. Pat. No. 7,064,244, issued Jun. 20, 2006; or in PCT Publication Nos. WO 92/03918, WO 02/12437, and in U.S. Pat. Nos. 5,814,318, and 5,570,429; also see Jakobovits et al., *Proc. Natl. Acad. Sci USA,* 90: 2551 (1993); Jakobovits et al., *Nature,* 362: 255 (1993); Bruggemann et al., *Year in Immunol.,* 7: 33 (1993); Pluschke et al., *Journal of Immunological Methods* 215: 27-37 (1998); Neuberger et al., *Nature* 338: 350-2 (1989); Lonberg et al., *Int. Rev. Immunol.* 13(1):65-93 (1995); and Bruggemann et al., *Curr. Opin. Biotechnol.,* 8(4): 455-8 (1997); and Kuroiwa et al., *Nature Biotech* 20(9): 889-894 (2002) the disclosures of which is hereby incorporated by reference in their entirety. The transgenic animals, B-cells or cell lines generated thereof, and the relevant methodologies disclosed therein also form an aspect of this invention.

The transgenes or transgene constructs may be introduced into the animal's genome by a variety of techniques including microinjection of pronuclei, transfection, nuclear transfer cloning, sperm-mediated gene transfer, testis-mediated gene transfer, and the like.

In one embodiment, the human Igα and/or Igβ gene, is preferably expressed in the B-cells of the transgenic animal by means of an immune-specific promoter, preferably a B-cell specific promoter. This human Igα or Igβ gene expression happens preferably within B-cells alone, leading to enhanced B-cell development and survival of the non-human transgenic animal. By "B-cell specific promoter" is meant the promoter/enhancers sequence of any B-cell specific genes, and/or variants or engineered portions thereof, that normally controls the expression of genes expressed in a B-cell, examples of which include, but are not limited to, promoters/enhancers of CD19, CD20, CD21, CD22, CD23, CD24, CD40, CD72, Blimp-1, CD79b (also known as B29 or Ig beta), mb-1 (also known as Ig alpha), tyrosine kinase blk, VpreB, immunoglobulin heavy chain, immunoglobulin kappa light chain, immunoglobulin lambda-light chain, immunoglobulin J-chain, etc. In a preferred embodiment, the CD79a, CD79b, or kappa light chain promoter/enhancer drives the B-cell specific expression of the human Igα and/or Igβ genes.

In yet another embodiment, the transgene construct comprising the nucleic acid molecule encoding the human Igα and/or Igβ genes is coexpressed with the transgene construct comprising an exogenous immunoglobulin or immunoglobulin (Ig) chain transgene locus. In this embodiment, both the Ig transgene locus and the human Igα and/or Igβ transgene may be present on the same transgenic expression vector or on two different transgenic expression vectors. In the latter case, the two transgenic expression vectors may be introduced into the non-human transgenic animal either at the same time or sequentially.

In accordance with this invention, variants of the human full length or extracellular domain alone, of Igα or Igβ are included herein. By this is meant nucleic acid sequences that allow for the degeneracy of the genetic code, nucleic acid sequences that encode for a polypeptide sequence that comprises amino acid substitutions of functionally equivalent residues and/or mutations that enhance the functionality of the extracellular domain. "Functionality of the extracellular domain" includes, but is not limited to, formation of a BCR capable of signal transduction.

By allowing for the degeneracy of the genetic code, the invention encompasses sequences that have at least about 70%, more usually about 80 to 85%, preferably at least about 90% and most preferably about 95% sequence identity to the extracellular polypeptide sequence of human Igα and human Igβ.

The term biologically functional equivalent is well understood in the art and is further defined in detail herein. Accordingly, sequences that have between about 70% and about 80%; or more preferably, between about 81% and about 90%; or even more preferably, between about 91% and about 99% identical at the amino acid level are considered functionally equivalent to human Igα and Igβ, provided the biological activity of the proteins is maintained.

The term functionally equivalent codon is used herein to refer to codons that encode the same amino acid, such as the six codons for arginine or serine, and also refers to codons that encode biologically equivalent amino acids.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below.

In making such changes, the hydropathic index of amino acids may also be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0.+−0.1); glutamate (+3.0.+−0.1); serine (+0.3); asparagine (+0.2) glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within .+−0.2 is preferred, those that are within .+−0.1 are particularly preferred, and those within .+−.0.5 are even more particularly preferred.

As outlined herein, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure (Johnson 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outlined above, to engineer second generation molecules having many of the natural properties of human Igα or Igβ with altered and improved characteristics.

Thus, variant nucleic acid sequences that encode for human Igα or Igβ and functionally equivalent polypeptides of human Igα or Igβ are useful in this invention.

The transgenic vectors containing the genes of interest may be introduced into the recipient cell or cells and then integrated into the genome of the recipient cell or cells by random integration or by targeted integration.

For random integration, a transgenic vector containing a human Igα or Igβ can be introduced into an animal recipient cell by standard transgenic technology. For example, a transgenic vector can be directly injected into the pronucleus of a fertilized oocyte. A transgenic vector can also be introduced by co-incubation of sperm with the transgenic vector before fertilization of the oocyte. Transgenic animals can be developed from fertilized oocytes. Another way to introduce a transgenic vector is by transfecting embryonic stem cells and subsequently injecting the genetically modified embryonic stem cells into developing embryos. Alternatively, a transgenic vector (naked or in combination with facilitating reagents) can be directly injected into a developing embryo. Ultimately, chimeric transgenic animals are produced from the embryos which contain the human(ized) Ig transgene integrated in the genome of at least some somatic cells of the transgenic animal.

In a particular embodiment, a transgene containing a human Igα or Igβ is randomly integrated into the genome of recipient cells (such as fertilized oocyte or developing embryos) derived from animal strains with an impaired expression of endogenous Igα or Igβ. The use of such animal strains permits preferential expression of immunoglobulin molecules from the human(ized) transgenic Ig locus. Alternatively, transgenic animals with human(ized) Igα and/or Igβ transgenes can be mated with animal strains with impaired expression of endogenous Igα and/or Igβ. Offspring homozygous for impaired Igα and/or Igβ and human(ized) Igα and/or Igβ can be obtained. Alternatively, expression of endogenous Igα and/or Igβ may be inhibited or lowered using antisense technology, intracellular anti-Igα and/or Igβ expression, and the like. In one embodiment, the method of choice for the knocking down the endogenous production of Igα and/or Igβ of the host animal is the RNA interference ($RNA_i$) method, which introduces either double-stranded RNA (ds RNA) or more preferably, short or small interfering RNA duplexes (siRNA) into the B-cells having intracellular host animal Igα and/or Igβ nucleic acid sequences. This can be achieved using commercially available kits, including but not limited to, Block iT™ or Stealth™ RNA kits from Invitrogen Corp.

For targeted integration, a transgenic vector can be introduced into appropriate animal recipient cells such as embryonic stem cells or already differentiated somatic cells. Afterwards, cells in which the transgene has integrated into the animal genome and has replaced the corresponding endogenous gene by homologous recombination can be selected by standard methods (See for example, Kuroiwa et al, Nature Genetics 2004, June 6). The selected cells may then be fused with enucleated nuclear transfer unit cells, e.g. oocytes or embryonic stem cells, which are totipotent and capable of forming a functional neonate. Fusion is performed in accordance with conventional techniques which are well established. Enucleation of oocytes and nuclear transfer can also be performed by microsurgery using injection pipettes. (See, for example, Wakayama et al., *Nature* (1998) 394:369.) The resulting egg cells are then cultivated in an appropriate medium, and transferred into synchronized recipients for generating transgenic animals. Alternatively, the selected genetically modified cells can be injected into developing embryos which are subsequently developed into chimeric animals.

Further, according to the present invention, a transgenic animal capable of producing human(ized) Igα and/or Igβ can also be made by introducing into a recipient cell or cells, one or more of the recombination vectors described herein above, one of which carries a human Igα and/or Igβ gene segment, linked to 5' and 3' flanking sequences that are homologous to the flanking sequences of the endogenous Igα and/or Igβ gene segment, then selecting cells in which the endogenous Igα and/or Igβ gene segment is replaced by the human Igα and/or Igβ gene segment by homologous recombination, and deriving an animal from the selected genetically modified recipient cell or cells.

Similar to the target insertion of a transgenic vector, cells appropriate for use as recipient cells in this approach include embryonic stem cells or already differentiated somatic cells. A recombination vector carrying a human Igα and/or Igβ gene segment can be introduced into such recipient cells by any feasible means, e.g., transfection. Afterwards, cells in which the human Igα and/or Igβ gene segment has replaced the corresponding endogenous Igα and/or Igβ gene segment by homologous recombination, can be selected by standard methods. These genetically modified cells can serve as nuclei donor cells in a nuclear transfer procedure for cloning a transgenic animal. Alternatively, the selected genetically modified embryonic stem cells can be injected into developing embryos which can be subsequently developed into chimeric animals.

In a specific embodiment, the transgene constructs of the invention may be introduced into the transgenic animals during embryonic life by directly injecting the transgenes into the embryo or indirectly by injecting them into the pregnant mother or into the egg-laying hen. Transgenic animals produced by any of the foregoing methods form another embodiment of the present invention. The transgenic animals have at least one, i.e., one or more, human(ized) Igα and/or Igβ gene in the genome, from which a functional human(ized) Igα and/or Igβ protein can be produced.

Further, the transgene constructs of the invention, namely, the human or humanized Igα and/or Igβ transgene and the humanized immunoglobulin transgene, are preferably expressed against a knockout background of either one, or more preferably both, the endogenous Ig, as well as the endogenous Igα and/or Igβ knockouts. Thus the transgenic animals of the present invention are capable of rearranging the human(ized) Ig loci and efficiently expressing a functional repertoire of human(ized) antibodies against a background that has substantially reduced endogenous Ig expression and more preferably, substantially reduced endogenous Igα and/or Igβ as well. In this context, by "substantially" is meant the degree of endogenous production, of either endogenous Ig expression alone or additionally, endogenous Igα and/or Igβ expression is reduced preferably at least about 30%-49%, or more preferably at least about 50%-79%, or even more preferably at least about 80-89%, or most preferably by about 90-100%.

The present invention provides transgenic rabbits expressing one or more human(ized) Ig loci and human(ized) Igα and/or Igβ, that are capable of rearranging and gene converting the human(ized) Ig loci, and expressing a functional repertoire of human(ized) antibodies. Preferably, these rabbits, additionally, do not produce substantial amounts of functional endogenous, rabbit immunoglobulins or functional endogenous, rabbit Igα and/or Igβ.

The present invention also provides other large transgenic animals, including but not limited to, birds, rodents and farm animals like cows, pigs, sheep, goats, donkeys, horses and the like expressing one or more human(ized) Ig loci and human(ized) Igα and/or Igβ. Again, preferably, these animals, additionally, do not produce substantial amounts of functional endogenous, immunoglobulins or functional endogenous, Igα and/or Igβ. Thus, these transgenic animals are capable of rearranging the human(ized) Ig loci and efficiently expressing a functional repertoire of human(ized) antibodies, with increased yields.

The invention is also directed to B-cells isolated from the different types of transgenic animals described above, that express the human(ized) Igα and/or Igβ gene and the human(ized) immunoglobulin loci. Further, such B-cells can be immortalized using conventional methods known and used by skilled artisans in the field, including but not limited to, using viral transformation, etc.

Immunization with antigen leads to the production of human(ized) antibodies against the same antigen in said transgenic animals.

Although preferred embodiments of the present invention are directed to transgenic animals having human(ized) Ig loci, it is to be understood that transgenic animals having primatized Ig loci and primatized polyclonal antisera are also within the spirit of the present invention. Similar to human(ized) polyclonal antisera compositions, primatized polyclonal antisera compositions are likely to have a reduced immunogenicity in human individuals.

Once a transgenic non-human animal capable of producing diversified human(ized) immunoglobulin molecules is made (as further set forth below), human(ized) immunoglobulins and human(ized) antibody preparations against an antigen can be readily obtained by immunizing the animal with the antigen. A variety of antigens can be used to immunize a transgenic host animal. Such antigens include, microorganism, e.g. viruses and unicellular organisms (such as bacteria and fungi), alive, attenuated or dead, fragments of the microorganisms, or antigenic molecules isolated from the microorganisms.

Preferred bacterial antigens for use in immunizing an animal include purified antigens from *Staphylococcus aureus* such as capsular polysaccharides type 5 and 8, recombinant versions of virulence factors such as alpha-toxin, adhesin binding proteins, collagen binding proteins, and fibronectin binding proteins. Preferred bacterial antigens also include an attenuated version of *S. aureus, Pseudomonas aeruginosa, enterococcus, enterobacter*, and *Klebsiella pneumoniae*, or culture supernatant from these bacteria cells. Other bacterial antigens which can be used in immunization include purified lipopolysaccharide (LPS), capsular antigens, capsular polysaccharides and/or recombinant versions of the outer membrane proteins, fibronectin binding proteins, endotoxin, and exotoxin from *Pseudomonas aeruginosa, enterococcus, enterobacter*, and *Klebsiella pneumoniae*.

Preferred antigens for the generation of antibodies against fungi include attenuated version of fungi or outer membrane proteins thereof, which fungi include, but are not limited to, *Candida albicans, Candida parapsilosis, Candida tropicalis*, and *Cryptococcus neoformans*.

Preferred antigens for use in immunization in order to generate antibodies against viruses include the envelop proteins and attenuated versions of viruses which include, but are not limited to respiratory synctial virus (RSV) (particularly the F-Protein), Hepatitis C virus (HCV), Hepatitis B virus (HBV), cytomegalovirus (CMV), EBV, and HSV.

Therapeutic antibodies can be generated for the treatment of cancer by immunizing transgenic animals with isolated tumor cells or tumor cell lines; tumor-associated antigens which include, but are not limited to, Her-2-neu antigen (antibodies against which are useful for the treatment of breast cancer); CD19, CD20, CD22 and CD53 antigens (antibodies against which are useful for the treatment of B-cell lymphomas), (3) prostate specific membrane antigen (PMSA) (antibodies against which are useful for the treatment of prostate cancer), and 17-1A molecule (antibodies against which are useful for the treatment of colon cancer).

The antigens can be administered to a transgenic host animal in any convenient manner, with or without an adjuvant, and can be administered in accordance with a predetermined schedule.

After immunization, serum or milk from the immunized transgenic animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethyleneglycol.

The fractionated human(ized) antibodies may be dissolved or diluted in non-toxic, non-pyrogenic media suitable for intravenous administration in humans, for instance, sterile buffered saline.

The antibody preparations used for administration are generally characterized by having immunoglobulin concentrations from 0.1 to 100 mg/ml, more usually from 1 to 10 mg/ml. The antibody preparation may contain immunoglobulins of various isotypes. Alternatively, the antibody preparation may contain antibodies of only one isotype, or a number of selected isotypes.

For making a human(ized) monoclonal antibody, spleen cells are isolated from the immunized transgenic animal whose B-cells expressing the animal's endogenous immunoglobulin have been depleted. Isolated spleen cells are used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1 ("Method For Generating Monoclonal Antibodies From Rabbits"), U.S. Pat. No. 4,977,081 ("Stable Rabbit-Mouse Hybridomas And Secretion Products Thereof"), WO 97/16537 ("Stable Chicken B-cell Line And Method of Use Thereof"), and EP 0 491 057 B1 ("Hybridoma Which Produces Avian Specific Immunoglobulin G"), the disclosures of which are incorporated herein by reference. In vitro production of monoclonal antibodies from cloned cDNA molecules has been described by Andris-Widhopf et al., "Methods for the generation of chicken monoclonal antibody fragments by phage display", *J Immunol Methods* 242:159 (2000), and by Burton, D. R., "Phage display", *Immunotechnology* 1:87 (1995), the disclosures of which are incorporated herein by reference.

In most instances the antibody preparation consists of unmodified immunoglobulins, i.e., human(ized) antibodies prepared from the animal without additional modification, e.g., by chemicals or enzymes. Alternatively, the immunoglobulin fraction may be subject to treatment such as enzymatic digestion (e.g. with pepsin, papain, plasmin, glycosidases, nucleases, etc.), heating, etc, and/or further fractionated to generate "antibody fragments".

The present invention also includes pharmaceutical compositions or antibody preparations comprising the antibodies or their fragments obtained by the methods defined above. The term "pharmaceutically acceptable ingredient" or "formulation" as used herein is intended to encompass a product comprising the claimed active ingredient(s), namely human (ized) antibody or antibody fragment, in specified amounts, as well as any product which results, directly or indirectly, from the combination of the specified active ingredient(s) in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the "pharmaceutical compositions" of the present invention encompass any composition made by admixing any active compound of the present invention and a pharmaceutically acceptable carrier.

The terms "administration of" and or "administering a" compound should be understood to mean providing any active compound of the invention, in any formulation, to an individual in need of treatment.

The pharmaceutical compositions for the administration of the compounds of this invention may conveniently be presented in dosage unit form and may be prepared by methods well known in the art of pharmacy. Suitable methods and carriers for use are those that are well-described in the art, and for example, in Remington, The Science and Practice of Pharmacy, ed. Gennaro et al., 20th Ed. (2000), although the skilled artisan in the field of immunology will readily recognize that other methods are known and are suitable for preparing the compositions of the present invention. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active ingredient is included in an effective amount, discussed above, sufficient to produce the desired effect upon the process or condition of diseases. Furthermore, formulations for the controlled, prolonged release of antibody molecules have been described in U.S. Pat. No. 6,706,289, whose methods are incorporated by reference herein.

Thus, the transgenic constructs, the vectors comprising the transgene constructs and the transgenic animals generated using the methods described above are all embodiments of the invention.

The invention is further illustrated, but by no means limited, by the following examples.

Example 1

Transfection of a Rabbit B-Cell Line with Human Igα and Igβ

To demonstrate the effect of human Igα and Igβ on the expression of human mIgM in rabbit B-cells, such cells are transfected with expression vectors encoding human Igα or Igβ or a human mIgM.

Human Igα and human Igβ and human IgM encoding genes are cloned in expression vectors.

An immortalized rabbit B-cell line is transfected with the expression vectors and cultured in medium in the presence of neomycin for the selection of stable transfectants. Resistant cells are analyzed by flow cytometry using antibodies specific for human IgM and human Igα and/or Igβ. Transfection of rabbit B-cells with an expression vector encoding human IgM results in low cell surface expression of human IgM. Cotransfection with human Igα and/or Igβ results in high cell surface expression of human mIgM. This demonstrates that human Igα and/or Igβ is necessary and sufficient for high cell surface expression of human(ized) or chimeric mIgM.

Example 2

Transfection of a B-Cell Line Derived from any Animal with Human Igα and Igβ

To demonstrate the effect of human Igα and Igβ on the expression of human mIgM in animal derived B-cells, expression vectors encoding human Igα or Igβ or a human mIgM are transfected in B-cell derived from chicken (DT40), cow, and pigs.

Immortalized B-cell lines are transfected with the expression vectors and cultured in medium in the presence of neomycin for the selection of stable transfectants. Resistant cells are analyzed by flow cytometry using antibodies specific for human IgM and human Igα and/or Igβ. Transfection of rabbit B-cells with an expression vector encoding human IgM results in low cell surface expression of human IgM. Cotransfection with human Igα and/or Igβ results in high cell surface expression of human mIgM. This demonstrates that human Igα and/or Igβ, is necessary and sufficient for high cell surface expression of human(ized) or chimeric mIgM.

Example 3

Transgenic Rabbits Expressing the Humanized Immunoglobulin Light and/or Heavy Chain Transgene with or without Human Igα and/or Igβ

Transgenic rabbits were generated as described by Fan et al. (Pathol. Int. 49: 583-594, 1999). Briefly, female rabbits were superovulated using standard methods and mated with male rabbits. Pronuclear-stage zygotes were collected from oviduct and placed in an appropriate medium such as Dulbecco's phosphate buffered saline supplemented with 20% fetal bovine serum. The exogenous DNA (e.g., expression vectors containing human(ized) immunoglobulin locus or human Igα or human Igβ) were microinjected into the pronucleus with the aid of a pair of manipulators. Morphological surviving zygotes were transferred to the oviducts of pseudopregnant rabbits. Pseudopregnancy was induced by the injection of human chorionic gonadotrophin (hCG). Between about 0.1-1% of the injected zygotes developed into live transgenic rabbits. Integration of the transgene in the genome was confirmed by PCR and FISH.

The presence of antibodies containing human IgG and/or human kappa light chain antigenic determinants in the serum of transgenic founder rabbits was determined using an ELISA assay. Antibody expression on the surface of B-cells was analyzed by flow cytometry. Rabbits with a transgene encoding a human(ized) immunoglobulin heavy chain locus, expressed 1-10 ug/ml human IgM. Young animals (6-9 weeks) expressed 100-4000 ug/ml human IgG. However, the expression of human IgG declined rapidly to levels of 10-100 ug/ml. Flow cytometric analysis of B-cells in peripheral blood revealed a small population of human mIgM+ cells (1-2%). The appendix of young rabbits contained up to 10% human mIgM+ cells which disappeared rapidly with age.

Introduction of transgenes encoding human Igα and/or Igβ results in the expression of 100-2000 ug/ml human(ized) IgM in serum and stable expression of 2000-12000 ug/ml human(ized) IgG. In appendix 30-70% of lymphocytes are human(ized) mIgM+. In peripheral blood equivalent numbers of B-cells express rabbit and human(ized) mIgM or mIgG.

All references cited throughout the disclosure along with references cited therein are hereby expressly incorporated by reference.

While the invention is illustrated by reference to certain embodiments, it is not so limited. One skilled in the art will understand that various modifications are readily available and can be performed without substantial change in the way the invention works. All such modifications are specifically intended to be within the scope of the invention claimed herein.

What is claimed is:

1. A transgenic rabbit whose genome comprises:
    (a) a transgene construct encoding a full-length, human Igα subunit of SEQ ID NO: 1, under the control of a B-cell specific promoter/enhancer of CD79a;
    (b) a transgene construct encoding a full-length, human Igβ subunit of SEQ ID NO: 7, under the control of a B-cell specific promoter/enhancer of CD79b;
and
    (c) a transgene construct encoding an unrearranged human immunoglobulin heavy chain locus;
    wherein the resultant transgene products, as a result of the simultaneous expression of the transgene constructs (a)-(c), combine to form a human B-cell receptor complex, such that human CD79a, human CD79b and human IgM are simultaneously present on the surface of B cells of said transgenic rabbit.

2. The transgenic rabbit of claim 1, wherein said transgenic rabbit is further characterized by impaired expression of endogenous Igα and/or Igβ.

3. The transgenic rabbit of claim 2, wherein expression of endogenous Igα and/or Igβ is knocked down in said transgenic rabbit.

* * * * *

SEQUENCE LISTING

<160> NUMBER OF SEQ ID NOS: 12

<210> SEQ ID NO 1
<211> LENGTH: 226
<212> TYPE: PRT
<213> ORGANISM: Homo sapien

<400> SEQUENCE: 1

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
                20                  25                  30

Leu Trp Met His Lys Val Pro Ala Ser Leu Met Val Ser Leu Gly Glu
            35                  40                  45

Asp Ala His Phe Gln Cys Pro His Asn Ser Ser Asn Asn Ala Asn Val
        50                  55                  60

Thr Trp Trp Arg Ile Leu His Gly Asn Tyr Thr Trp Pro Pro Glu Phe
65                  70                  75                  80

```
Leu Gly Pro Gly Glu Pro Asn Gly Thr Leu Ile Ile Gln Asn Val
            85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
            115                 120                 125

Pro Pro Arg Pro Phe Leu Asp Met Gly Glu Gly Thr Lys Asn Arg Ile
130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
            165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
            195                 200                 205

Thr Tyr Gln Asp Val Gly Ser Leu Asn Ile Gly Asp Val Gln Leu Glu
            210                 215                 220

Lys Pro
225

<210> SEQ ID NO 2
<211> LENGTH: 65
<212> TYPE: PRT
<213> ORGANISM: Bos taurus

<400> SEQUENCE: 2

Glu Gln Ala Ser Pro Ile Ala Gly Val Glu Trp Gly Pro Val Thr Val
1               5                   10                  15

Glu Val Arg Leu Thr Gly Thr His Val Gln Ser Ser Val Met Tyr
            20                  25                  30

Arg Gly Asp Val Gly Ala Gly Glu Lys Pro Thr Arg Met Arg Gln Ser
            35                  40                  45

Asp Lys Lys Ile Arg Asp Leu Asn Ile Met Phe Ala Ile Gln Asp His
        50                  55                  60

Ala
65

<210> SEQ ID NO 3
<211> LENGTH: 66
<212> TYPE: PRT
<213> ORGANISM: Mus musculus

<400> SEQUENCE: 3

Leu Glu Ala Arg Leu Leu Leu Tyr Ala Cys Arg Val Glu Gly Gly Pro
1               5                   10                  15

Thr Asn Glu Arg Leu Thr Glu Asn Gly Arg Pro Ile Phe Ser Gln Ser
            20                  25                  30

Ile Val Pro Gln Gly Thr Thr Gln Phe Phe Pro Glu Asn Arg Leu Trp
            35                  40                  45

Gln Ile Asn Asn Ile Leu Lys Arg Asn Val Phe Val Met Pro Asp Asn
        50                  55                  60

His Ala
65

<210> SEQ ID NO 4
```

<211> LENGTH: 66
<212> TYPE: PRT
<213> ORGANISM: Canis

<400> SEQUENCE: 4

Leu Cys Thr Ile Gly Gly Ser Val Asp Gly Pro Met Thr Thr Arg
1               5                   10                  15

Leu Leu Arg Arg Leu Ser Ser Lys Leu Ile Val Gln Ala Asp Ile Ser
            20                  25                  30

Tyr Lys Gly Glu Thr Asp Thr Met Met Arg Gln Glu Lys Asp Leu Asn
            35                  40                  45

Gln Lys Ile Leu Ser Ser Glu Arg Leu Asn Met Phe Val Gln Asp His
50                  55                  60

Gly Asp
65

<210> SEQ ID NO 5
<211> LENGTH: 73
<212> TYPE: PRT
<213> ORGANISM: Pan

<400> SEQUENCE: 5

Ser Ala Val Arg Glu Trp Pro Ser Pro Gly Pro Tyr Ser His Cys Pro
1               5                   10                  15

Ala Gly Asp Thr Arg Phe Ile Phe Glu Val Gly Ile Glu Pro Ile Pro
            20                  25                  30

Ser Met Trp Val Ser Asn Arg Leu Gly Gln Arg Asp Gly His Ser Pro
            35                  40                  45

Leu Gln Lys Val Ser Pro Leu Gly Pro Leu Ser Gln Pro Gly Glu Gly
50                  55                  60

Leu Gly Arg Gly Thr Pro Asn Ala Gln
65                  70

<210> SEQ ID NO 6
<211> LENGTH: 2
<212> TYPE: PRT
<213> ORGANISM: Oryctolagus cuniculus

<400> SEQUENCE: 6

Asp His
1

<210> SEQ ID NO 7
<211> LENGTH: 229
<212> TYPE: PRT
<213> ORGANISM: Homo sapien

<400> SEQUENCE: 7

Met Ala Arg Leu Ala Leu Ser Pro Val Pro Ser His Trp Met Val Ala
1               5                   10                  15

Leu Leu Leu Leu Leu Ser Ala Glu Pro Val Pro Ala Ala Arg Ser Glu
            20                  25                  30

Asp Arg Tyr Arg Asn Pro Lys Gly Ser Ala Cys Ser Arg Ile Trp Gln
            35                  40                  45

Ser Pro Arg Phe Ile Ala Arg Lys Arg Phe Thr Val Lys Met His
50                  55                  60

Cys Tyr Met Asn Ser Ala Ser Gly Asn Val Ser Trp Leu Trp Lys Gln
65                  70                  75                  80

Glu Met Asp Glu Asn Pro Gln Gln Leu Lys Leu Glu Lys Gly Arg Met

```
                        85                  90                  95
Glu Glu Ser Gln Asn Glu Ser Leu Ala Thr Leu Thr Ile Gln Gly Ile
                100                 105                 110
Arg Phe Glu Asp Asn Gly Ile Tyr Phe Cys Gln Gln Lys Cys Asn Asn
            115                 120                 125
Thr Ser Glu Val Tyr Gln Gly Cys Gly Thr Glu Leu Arg Val Met Gly
        130                 135                 140
Phe Ser Thr Leu Ala Gln Leu Lys Gln Arg Asn Thr Leu Lys Asp Gly
145                 150                 155                 160
Ile Ile Met Ile Gln Thr Leu Leu Ile Ile Leu Phe Ile Ile Val Pro
                165                 170                 175
Ile Phe Leu Leu Leu Asp Lys Asp Asp Ser Lys Ala Gly Met Glu Glu
                180                 185                 190
Asp His Thr Tyr Glu Gly Leu Asp Ile Asp Gln Thr Ala Thr Tyr Glu
                195                 200                 205
Asp Ile Val Thr Leu Arg Thr Gly Glu Val Lys Trp Ser Val Gly Glu
210                 215                 220
His Pro Gly Gln Glu
225

<210> SEQ ID NO 8
<211> LENGTH: 51
<212> TYPE: PRT
<213> ORGANISM: Canis

<400> SEQUENCE: 8

Gly Val His Asn Leu Val Gly Lys Thr His Gln Asp Thr Gly Gly Ala
1               5                   10                  15
Val Glu Ile Arg His Thr Lys Asp Val Ala Arg Leu Glu Lys Pro Pro
            20                  25                  30
Arg Asp Leu Leu Gln Asp Val Gln Ser Ser Lys Gly Ser Phe Ser Lys
        35                  40                  45
Arg Asp Asn
    50

<210> SEQ ID NO 9
<211> LENGTH: 70
<212> TYPE: PRT
<213> ORGANISM: Rattus

<400> SEQUENCE: 9

Thr Val Cys Leu Met Phe Gly Met Thr Lys Ser Gln Pro Pro Ile Phe
1               5                   10                  15
Gln Pro Lys His Ala Lys Ser Ser Met Phe His Thr Asp Tyr Val Met
            20                  25                  30
Thr Phe Arg Gln Lys Gly Asn Gln Arg Glu Phe Pro Asp His Ile Ser
        35                  40                  45
Gln Thr Arg Gly Val Tyr Leu Asn Gln Tyr Ser Thr Glu Pro Asp Thr
    50                  55                  60
Asp Leu Leu Asp Arg Asn
65                  70

<210> SEQ ID NO 10
<211> LENGTH: 71
<212> TYPE: PRT
<213> ORGANISM: Bos taurus
```

<400> SEQUENCE: 10

Gly Ser Ile Gly Leu Asn Asn Leu Leu Gly Gly Lys Leu Asp Lys Thr
1               5                   10                  15

Asp Leu Asp Asn Thr His Val Lys Gly Ser Glu Ile Arg His Val
            20                  25                  30

Glu Asp Asp Leu Phe Arg Pro Lys Pro Ser Glu Lys Thr His Ala Gln
        35                  40                  45

Ile Leu Gln His Lys Glu Val Leu Ser Val Gln Gln Lys Glu Ala Lys
    50                  55                  60

Gly Gln Arg Thr Glu His Arg
65                  70

<210> SEQ ID NO 11
<211> LENGTH: 70
<212> TYPE: PRT
<213> ORGANISM: Mus musculus

<400> SEQUENCE: 11

Thr Val Ser Met Cys Leu Leu Phe Phe Gly Met Thr Ser Leu Pro Leu
1               5                   10                  15

Phe Gln Pro Gln His Ala Lys Ser Ser Met Phe Thr His Ala Leu Thr
            20                  25                  30

Phe Arg Arg Gly Ser Gln Gln Glu Val Ser Glu Ile Val Gln Thr Gly
        35                  40                  45

Val Tyr Asn Gln Tyr Lys Asp Ser Ala Asn His Asn Thr Asp Ser Leu
    50                  55                  60

Leu Asp Arg Leu Gly Asn
65                  70

<210> SEQ ID NO 12
<211> LENGTH: 139
<212> TYPE: PRT
<213> ORGANISM: Gallus

<400> SEQUENCE: 12

Met Gly Asp Phe Cys Arg Arg Leu Trp Val Leu Gln Val Asn Trp Met
1               5                   10                  15

Ala Ala Ala Gly Gly Ile Pro Thr Asp Gly Asn Ser Thr Ser Arg Thr
            20                  25                  30

Glu Val Gly Met His Tyr Ala Lys Asn Thr Ser His Phe Ile Thr Ser
        35                  40                  45

Gln Pro His Ala Met Gln Tyr Lys Ala Leu Gly Asn Gly Lys Glu Phe
    50                  55                  60

His Val Asp Gln Ser Ser Asp Phe Ser Ile Asn Thr Asn Asp Arg
65                  70                  75                  80

Ile Ser Phe Ser Arg Ser Tyr Val Asp Ser Asn Leu Thr Glu Glu Lys
            85                  90                  95

Arg Gln Pro Asn Ser Ile Ser Arg Asn Ile Gln Ile Gln Asn Thr Ile
            100                 105                 110

Ile Leu Val Ile Ser Met Leu Phe Glu Gly Arg Glu Arg Pro Glu Val
        115                 120                 125

Glu Ile Thr Pro Phe Asp Met Lys Ala Thr Glu
    130                 135